United States Patent [19]

Akiyama

[11] Patent Number: 5,523,320
[45] Date of Patent: Jun. 4, 1996

[54] N-METHYLDEACETYLCOLCHICEINAMIDE DERIVATIVES

[75] Inventor: Kiyoshi Akiyama, Komatsu, Japan

[73] Assignee: Ohgen Research Laboratories, Ltd., Ishikawa-ken, Japan

[21] Appl. No.: 367,999

[22] Filed: Jan. 3, 1995

Related U.S. Application Data

[63] Continuation of Ser. No. 49,851, Apr. 23, 1993, abandoned.

[30] Foreign Application Priority Data

Jan. 20, 1993 [JP] Japan ................................. 5-024754

[51] Int. Cl.[6] ........................ A61K 31/16; A61K 31/335; C07C 233/23; C07D 309/10
[52] U.S. Cl. .................. 514/459; 514/467; 514/534; 514/546; 514/625; 549/417; 549/450; 549/452; 560/107; 560/250; 564/202
[58] Field of Search .................... 549/450, 452, 549/417; 564/202; 560/250, 107; 514/459, 467, 625, 534, 546; 536/18.7

[56] References Cited

U.S. PATENT DOCUMENTS 5,220,002  6/1993  Akiyama ................................ 514/629
5,326,786  7/1994  Akiyama ................................ 514/467

FOREIGN PATENT DOCUMENTS 493064    7/1992  European Pat. Off. .
WO91/02084 2/1991  WIPO .
WO92/15291 9/1992  WIPO .

OTHER PUBLICATIONS van Temelen et al., "The Synthesis of Colchicine", Tetrahedron, 1961, vol. 14, pp. 8–34, Pergamon Press.
Leiter et al., "Damage Induced in Sarcoma 37 with Chemical Agents. IV. Derivatives of Colchiceinamide[1]", Journal of the National cancer–Institute, 13, pp. 731–739 (1952).
Davis, "Microbial Transformations of N-Methylcolchiceinamide", Antimicrobial Agents and Chemotherapy, Mar. 1981, vol. 19, No. 3, pp. 465–469.
Hartwell et al., "N–Substituted Colchicainamides", J. Am. Chem. Soc., vol. 74, pp. 3180–3181 (1952).
Raffauf et al., J. Am. Chem. Soc., vol. 75, pp. 5292–5294. (1953).
Chem. Engng. News, "Demecolcine", vol. 37, No. 41, p. 67 (1957).
Martin et al., Cancer Research, 4b, 2189–2192 (1986).
Quinn et al., C.A., 94:167,463f (1981).

Primary Examiner—Nicky Chan
Attorney, Agent, or Firm—Wenderoth, Lind & Ponack

[57] ABSTRACT

N-methyldeacetylcolchiceinamide derivatives represented by the formula

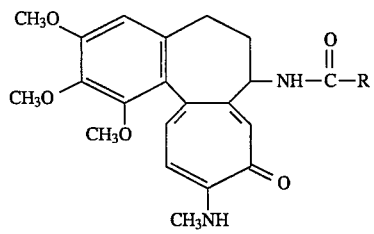

wherein R denotes a residue obtained by removing COOH from a $C_3$–$C_7$ sugar carboxylic acid, and hydroxyl groups present in the residue may properly be protected with a protecting group for a hydroxyl group.

The N-methyldeacetylcolchiceinamide derivatives have less toxicity and strong effect for inhibiting proliferation of tumor cells, and are expected to be used as a carcinostatic.

5 Claims, No Drawings

N-METHYLDEACETYLCOLCHICEINAMIDE DERIVATIVES

This application is a continuation of now abandoned application Ser. No. 08/049,851 filed Apr. 23, 1993, now abandoned.

This invention relates to novel N-methyldeacetylcolchiceinamide derivatives, and more detailedly, relates to N-methyldeacetylcolchiceinamide derivatives represented by the following formula and salts thereof:

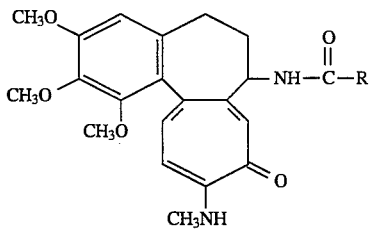

(I)

wherein R denotes a residue obtained by removing COOH from a $C_3$–$C_7$ sugar carboxylic acid, and hydroxyl groups present in the residue may properly be protected with a protecting group for a hydroxyl group.

It is already known that colchicine represented by the following formula

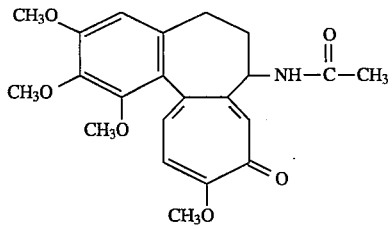

(A)

has pharmacological actions on cancer cells, gout, etc. (E. E. Van Tamelen, T. A. Spencer, Jr., D. S. Allen, Jr. and R. L. Orvis, Tetrahedron, 14, 8 (1961)).

However, colchicine has strong toxicity and has utterly been disregarded after emergence of demecolchicine [Deacetyl-N-methylcolchicine; Chem. Engng. News. 37, Nos. 41 and 67 (1959)] which was subsequently found.

The present inventors sought colchicine derivatives having only low toxicity and a further excellent carcinostatic action, and found, that deacetylcolchicine derivatives presented by the following formula

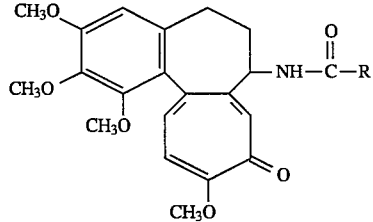

(B)

wherein R is as defined above, exhibit a strong effect to inhibit cell proliferation on cancer cells, and proposed them (refer to EP-A-493,064).

On the other hand, it is also already known that colchiceinamide represented by the following formula

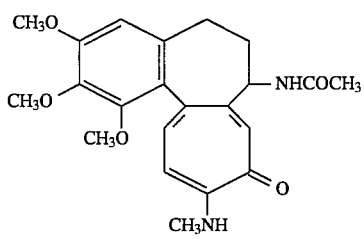

(C)

has pharmacological actions on cancer cells [Journal of the National Cancer Institute, 13, 731–739 (1952)].

The present inventors intensely studied to find colchicine derivatives and their related compounds having further reduced toxicity and a further excellent carcinostatic action, and as a result they have now found, that N-methyldeacetylcolchiceinamide derivatives represented by the above formula (I) and obtained by substituting a methylamino group for the methoxy group at the 10-Position of compounds of the above formula (B) also have reduced toxicity and exhibit a strong effect to inhibit cell proliferation on cancer cells and are expected to be used as a carcinostatic, and thus completed this invention.

Examples of "a residue obtained by removing COOH from a $C_3$–$C_7$ sugar carboxylic acid" represented by R in the above formula (I) are monovalent residues obtained by removing COOH from 3–7 monosaccharide carboxylic acids such as glyceric acid, ribose carboxylic acid, glucuronic acid, gluconic acid and glucoheptanoic acid (hereafter referred to as sugar residues), and specific examples are as follows.

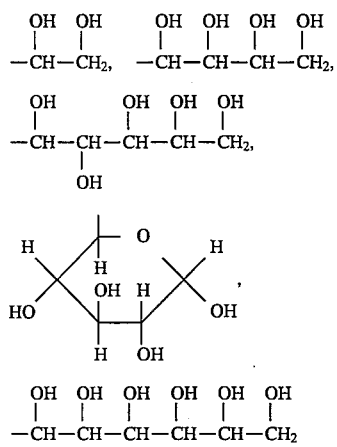

At least part of the plural hydroxyl groups existing in the thus described sugar residues may properly be protected with a protecting group for a hydroxyl group. Examples of the protecting group are acyl groups such as $C_1$–$C_{10}$ (preferably $C_2$–$C_6$) alkanoyl groups, e.g. acetyl, propionyl, butyryl and pivaloyl, and aroyl group, e.g. benzyol; and acetal and ketal groups represented by the formula

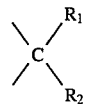

wherein $R_1$ denotes a hydrogen atom or an alkyl group and $R_2$ denotes a $C_1$–$C_6$ (preferably $C_1$–$C_4$) alkyl or a phenyl group, for example

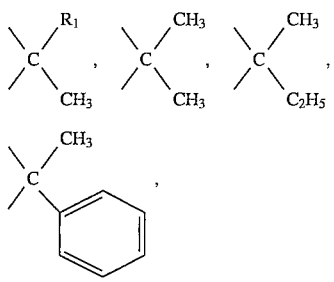

As preferred examples of R, there can be mentioned groups represented by the following formula

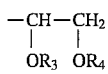

wherein $R_3$ and $R_4$ each denote a hydrogen atom or a protecting group for a hydroxyl group (for example an acyl group as above-mentioned), or $R_3$ and $R_4$ combine to denote a protecting group for hydroxyl groups (for example, an acetal or ketal group as above-mentioned).

Further, as salts of the N-methyldeacetylcolchiceinamide derivatives of the formula (I), there can, for example, be mentioned inorganic acid salts such as hydrochloride and sulfate; and organic acid salts such as acetate, propionate, butyrate, lactate, tartrate, malate, citrate, gluconate, succinate, maleate, fumarate, glytyllytinate, benzoate, etc.

A compound of the above formula (I) of this invention can, for example, be prepared by amidating N-methyldeacetylcolchiceinamide of the following formula

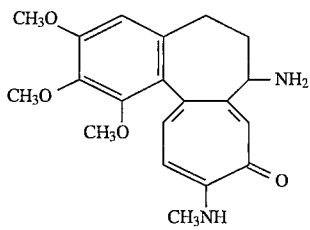

with a sugar carboxylic acid represented by the following formula

 (III)

wherein R is as defined above
or a reactive derivative thereof.

The amidation of N-methyldeacetylcolchiceinamide of the formula (II) with a sugar carboxylic acid of the formula (III) or an active derivative thereof can be carried out using amidation reaction known per se in peptide chemistry.

For example, a compound of this invention can be prepared by reacting N-methyldeacetylcolchiceinamide of the formula (II) with a halide of sugar carboxylic acid of the formula (III) in the presence of a base. The above reaction can be carried out generally at a temperature between about 0° C. and about 30° C., preferably at about 0° C to about room temperature. The amount of halide is not strictly limited, but it is convenient to use it in the range of usually 1 to 1.5 moles, particularly 1 to 1.2 moles per mole of N-methyldeacetylcolchiceinamide. Further, as bases, there can, for example, be used tertiary amines such as triethylamine and pyridine; alkali metal carbonates (bicarbonates) such as sodium carbonate, sodium bicarbonate, potassium carbonate and potassium bicarbonate; etc. Its use amount can be in the range of generally 1 to 1.5 moles, preferably 1 to 1.2 moles per mole of N-methyldeacetylcolchiceinamide.

The above reaction can usually be carried out in an inert solvent, and as usable solvents, there can, for example, be mentioned halogenated hydrocarbons such as methylene chloride, chloroform, carbon tetrachloride, dichloroethylene and trichloroethylene; aliphatic ethers such as ethyl ether and methyl cellosolve; aromatic hydrocarbons such as benzene and toluene; etc.

Further, a compound of this invention can also be prepared either by reacting directly N-methyldeacetylcolchiceinamide with a sugar carboxylic acid of the above formula (III) in the presence of a condensing agent such as DCC (dicyclohexylcarbodiimide) or by reacting N-methyldeacetylcolchiceinamide with an ester (for example methyl ester, ethyl ester, butyl ester or the like) of a sugar carboxylic acid of the above formula (III).

In the thus described reactions, N-methyldeacetylcolchiceinamide of the above formula (II) used as a starting raw material is a novel compound undisclosed in past literatures, and can, for example, be prepared by reacting deacetylcolchicine [Refer to J. Am. Chem. Soc., 75, 5292 (1952); EP-A-493,064] with methylamine according to the process disclosed in J. L. Hartwell, M. V. Nadkarni and J. Leiter: J. Am. Chem. Soc., 74, 3180 (1952), or by reacting colchicine with methylamine and hydrolyzing (deacetylatin) the resultant N-methylcolchiceinamide [refer to later-described Reference example 1].

A compound of the above formula (I) of this invention can further also be prepared by reacting a deacetylcolchicine derivative [refer to later-described Reference example 2]disclosed in the above EP-A-493,064 and represented by the following formula

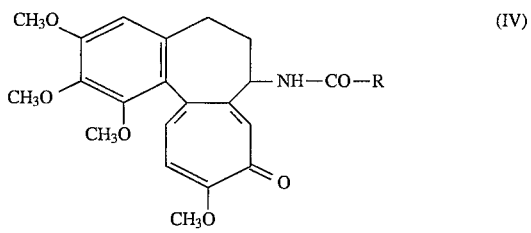

wherein R is as defined above, with methylamine to convert the methoxy group to a methylamino amino group.

The methylamination reaction of a compound of the formula (IV) can be carried out according to a process known per se [refer to Patrick J. Davis : Antimicrobial Agents and Chemotherapy, Mar. 1981, P465–469; J. L. Hartwell et al., J. Am. Chem. Soc., 74, 3180 (1952)], for example by reacting a compound of the formula (IV) with methylamine at a temperature between room temperature and the boiling point of the solvent, preferably about 40° C. and about 90° C.

Although the amount of methylamine used is not strictly limited, it is convenient to use it in the range of usually 2 to 30 moles, particularly 10 to 20 moles per mole of a compound of the formula (IV). The reaction is usually carried out in the presence of an aqueous medium in a closed vessel.

Compounds of this invention obtained by the thus described process can be separated and purified by methods known per se, for example, extraction, chromatography, crystallization or a combination thereof or the like.

A compound of this invention when there are protecting groups for hydroxyl groups in the sugar residue represented by R can, in some occasion, be subjected to a reaction for removal of the protective groups, for example hydrolysis, to eliminate the protective groups.

Further, the thus obtained N-methyldeacetvleolchieeinamide derivative of the formula (I) can, if necessary, be converted to such a salt as above-mentioned, according to a reaction known per se to form a salt, for example, by treating it with a suitable acid.

An N-methyldeacetylcolchiceinamide derivative of the above formula (I) obtained by this invention contains an asymmetric carbon atom at the side chain, and can exist in the D-form, L-form or DL-form.

As apparent from the following in vitro test on cancer cells, the N-methyldeacetylcolchiceinamide derivatives of the above formula (I) provided by this invention exhibit an excellent carcinostatic action.

Test example 1: In vitro cancer cell proliferation inhibiting text

Mouse leukemic cells p388/S and adriamycin-resistant mouse leukemic cells P388/ADR subculturally transplanted in the abdominal cavity of mice were taken out together with the asites therefrom, respectively, and after washing, suspended in RPMI 1640 media (each containing 10% fetal bovine serum and 10 µM 2-mercaptoethanol) to $2 \times 10^5$ cells/ml, respectively. 0.5 vol. % each of test solutions (solutions of the compound of the later-described in Example 1 in dimethylsulfoxide) were added to portions of each of these cell suspensions, respectively; and the mixtures were separately put into a 24-well culture plate and subjected to culture for 2 days in a 5% carbon dioxide culturing vessel. A 0.5% Trypan Blue solution was added to each of the cell culture broths in the same amount, and the 50% proliferation inhibitory concentration ($IC_{50}$) of the compound of Example 1 was determined by counting the number of the cells not stained as living cells under a microscope. The results of the experiment carried out three times are shown in the following Table 1.

TABLE 1

| Compound | Cytotoxicity $IC_{50}$ (ng/ml) | |
| --- | --- | --- |
| | P388/S | P388/ADR |
| Compound of | 3.2 | 9.2 |
| Example 1 | 4.2 | 11.0 |
| | 4.6 | 11.1 |

Test example 2: Acute toxicity test

Portions of test solutions (solutions obtained by dissolving the compound of the later-described Example 1 in 0.2N hydrochloric acid and then diluting the solution with physiological saline to the prescribed concentrations) were intraperitoneally administered to groups of CDF male mice, each group consisting of 8 mice, respectively, and body weights, symptoms, dates of death, etc. were observed for 10 days. Application amounts reduced at a common ratio of 1.3 were settled with 62 mg/kg as a maximum amount, the $LD_{50}$ value thereof was calculated using the Litchfield Wilcoxon method, and as a result, the $LD_{50}$ of the compound of the formula (I) was 41.0 mg/kg (35.8 to 46.9 mg/kg).

On acute toxicity symptoms, the lie of hair got worse on and after one day after administration, and in the groups of high dose, cases where diarrhea or constipation arose were observed. Further, among survival cases in the 47 mg/kg administration group, cases were observed which exhibited such walking problems as in the right leg and paralysis of one side of the body. Further, as for weight change, body weight, in each case, tended to decrease up to 2 to 4 days after administration, but thereafter increased gradually.

As apparent from the above test results, the compounds of this invention have a strong inhibitory action on cancer cells, and only comparatively low toxicity, and are expected to be used as a carcinostatic.

When a compound of this invention is used as a drug such as a carcinostatic, the compound can be administered orally or parenterally (for example, injected intravenously, intramuscularly, subcutaneously, or the like). Its effective dose can be varied over a wide range deending on the symptom, the degree of the disease, the weight and the age of a patient to which the compound is to be administered, judgment of the doctor, etc., but, for example in case of injection, can usually, be about 1 to about 5 mg/kg/day, and the compound can be administered once a day or in several divisions a day.

When a compound of this invention is used as a drug, an effective amount of the compound can be formulated together with pharmaceutically acceptable carriers or diluents (for example, excipients, solvents, other auxiliaries, etc.) into administration unit forms suitable for administration, for example, dosage forms such as tablets, powders, granules, capsules, enteric agents, troches syrups, elixirs, liquids, suspensions and emulsions.

As carriers or diluents usable for the above formulation, there can, for example, be mentioned excipients such as starch, lactose, sucrose, mannitol and carboxymethylcellulose; lubricants such as magnesium stearate, sodium lauryl sulfate and talc; binders such as dextrin, microcrystalline cellulose, polyvinylpyrrolidone, gum arabic, corn starch and gelatin; disintegrants such as potato starch and carboxymethylcellulose; diluents such as distilled water for injection, physiological saline, aqueous dextrose solutions, vegetable oils for injection, propylene glycol and polyethylene glycol; etc. and further if necessary, there can be compounded a flavor, a colorant, a tonicity agent, a stabilizer, an antiseptic, an agent to make a compound of this invention painless, etc.

Further, another pharmacologically active substance can, if necessary, be compounded in the drug of this invention.

This invention is more specifically described below according to examples.

Reference example 1: Preparation of N-methyldeacetyl colchiceinamide

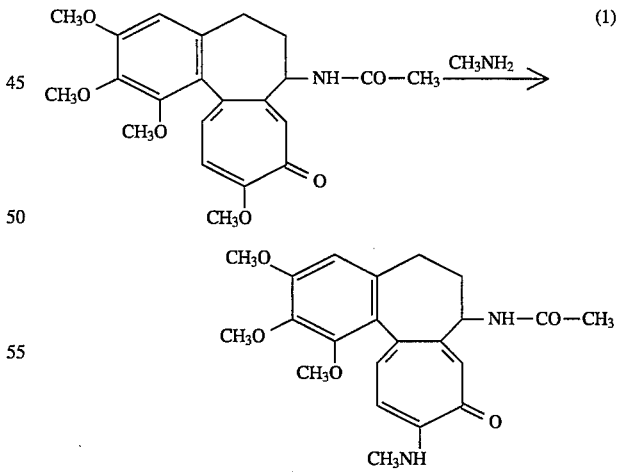

A mixed solution of colchicine (5.00 g, 12.5 mmoles), an aqueous 40methylamine solution (10 ml, 130 mmol) and ethyl alcohol (10 ml) was subjected to reaction at 120° C. for 20 hours under stirring in a sealed tube. The solvent was distilled off, water (10 ml) was added to the residue, and the mixture was extracted with chloroform. The chloroform layer was separated, washed with water and dried. The solvent was evaporated, and the residue was separated and purified by silica gel column chromatography [chloroform : methanol (20:1)]. Thereby, 4.20 g of N-methylcolchiceinamide was obtained as yellow crystals (yield 84%).

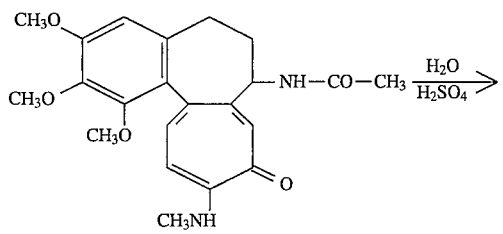

(2)

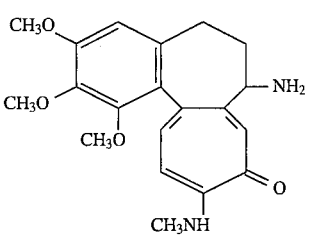

A mixed solution of N-methylcolchiceinamide (3.00 g, 7.5 mmoles), water (50 ml) and concentrated sulfuric acid (15 ml) was stirred at 100° C for 5 hours to cause hydrolysis (deacetylation reaction). The reaction solution was made alkaline with anhydrous sodium carbonate under ice cooling, and extracted with chloroform. The chloroform layer was separated, washed with water and dried. The solvent was evaporated to dryness. The residue was subjected to separation and purification by silica gel column chromatography [chloroform: methanol (20:1)]. Thereby, 2.20 g of N-methyldeacetylcolchiceinamide was obtained as yellow crystals.

Reference example 2

Preparation of N-(O,O-isopropylideneglyceroyl)deacetylcolchicine (IVa) [another name: deacetylcolchicine-glyceric acid acetonideamide]

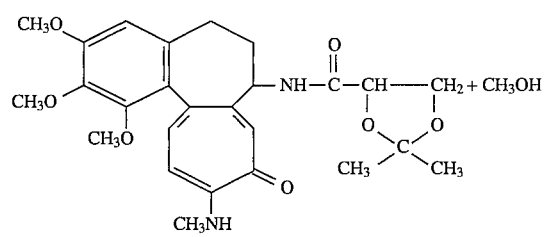

(IVa)

Potassium glyerate acetonide (3.60 g, 20 mmoles) was suspended in 30 ml of dry ether, and an ether (5 ml) solution of 2.40 g (20 mmols) of thionyl chloride was added dropwise to the suspension. After the dropwise addition, the mixture was refluxed for 3 hours. After the mixture was cooled to room temperature, the precipitate was filtered by suction, and the filtrate was concentrated under reduced pressure. Dry methylene chloride was added to the residue to dissolve it.

Meanwhile, 2.96 g (8.3 mmoles) of deacetylcolchicine and 2.02 g (20 mmols) of triethylamine were dissolved in 30 ml of methylene chloride. The mixture was cooled to 0° C., and the above methylene chloride solution of glyceric acid chloride was added dropwise. After stirring at 0° C. for 3 hours, the methylene chloride solution was washed with an aqueous sodium bicarbonate solution. The methylene chloride layer was dried over magnesium sulfate and then concentrated under reduced pressure. The residue was separated by silica gel column chromatography, and 1.11 g of the captioned compound (IVa-V: L-isomer) was obtained from a benzene-acetone (5:1) eluate. Yield 28%, m.p. 251 to 253° C. (decomposed).

Further, 0.58 g of a second captioned compound (IVa-2: D-isomer) was obtained from a benzene-acetone (5:2) eluate. Yield 14%.

EXAMPLE 1

Preparation of N-(O,O-isopropylideneglyceroyl)-N-methyldeacetylcolchiceinamide (Ia)

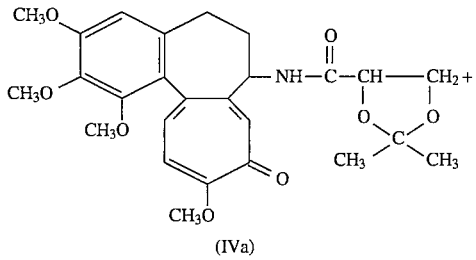

(IVa)

CH₃NH₂ →

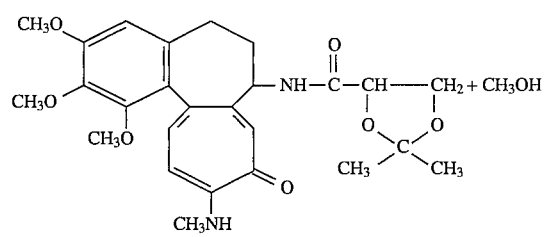

N-(O,O -isoproylideneglyceroyl)deacetylcolchicine (IVa) (2.74 g, 5.6 mmoles) and 10 ml of an aqueous methylamine solution (40%) were put into a sealed tube and stirred with heating to 75° to 80° C. for 20 hours. After completion of the reaction, the reaction mixture was concentrated in an evaporator and the residue was dissolved in chloroform. The chloroform layer was washed with saturated saline and dried over magnesium sulfate. Chloroform was distilled off under reduced pressure and the residue was subjected to separation and purification by silica gel column chrom atography. As a result, 1.93 of the desired compound (Ia) was obtained from the benzene-acetone (4:1) eluate. Yield: 70%

IR: 1660cm$^{-1}$ (C=O) NMR:δ=1.40, 1.44 (3H,s), 1.49, 1.69 (3H,s,), 1.85–1.95 (2H,m), 2.17–2.54 (3H,m), 3.07 (3H,d), 3.61 (3H,s), 3.89 (3H,s), 3.94 (3H,s), 3.99–4.06 (1H,m), 4.18–4.29 (1H,m), 4.41–4.51 (1H,m), 4.63–4.72 (1H,m), 6.54 (1H,s) 7.05–7.44 (3H,m)

EXAMPLE 2

Preparation of N'-(O,O-isopropylideneglyceroyl)-N-methyldeacetyleolehieeinamide (Ia)

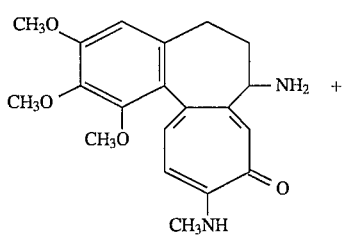

-continued

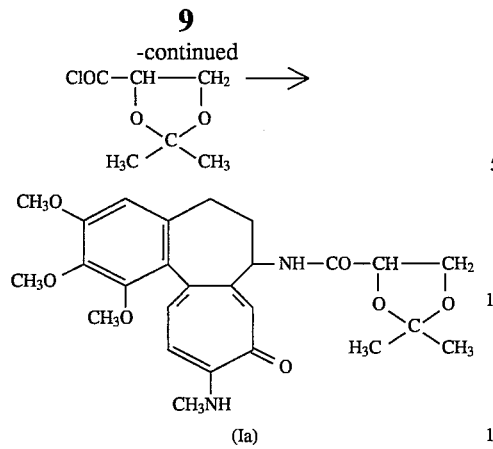

(Ia)

Potassium glyerate acetonide (3.60 g, 20 mmoles) was suspended in dry ether (30 ml), and an ether (5 ml) solution of 2.40 g (20 mmoles) thionyl chloride was added dropwise. After the dropwise addition, the mixture was refluxed for 3 hours. The mixture was cooled to room temperature, the formed precipitate was filtered by suction, and the filtrate was concentrated under reduced pressure. Dry chloroform was added to the residue to dissolve it.

Meanwhile, 2.96 g (8.3 mmoles) of N-methyldeacetyl-colchiceinamide and 2.02 g (20 mmols) of triethylamine were dissolved in 30 ml of chloroform. The mixed solution was cooled to 0° C., and the above glyceric acid acetonide chloride solution was added dropwise. The resultant chloroform solution was stirred at 0° C. for 3 hours, and then washed with an aqueous sodium bicarbonate solution. The chloroform layer was dried over anhydrous magnesium sulfate and concentrated under reduced pressure. The residue was subjected to separation and purification by silica gel column chromatography. As a result, 1.81 g of the desired compound (Ia) was obtained from a benzene-acetone (4:1) eluate. Yield 45%.

EXAMPLE 3

Preparation of an injection 2.0 g of N'-(O,O-isopropylideneglyceroyl)-N-methyldeacetylcolchiceinamide was dissolved in 1L of distilled water for injection at ordinary temperature, the solution was made isotonic with sodium chloride, and the mixture was put into ampoules which were then sealed. 1 ml of this injection contains 2 mg of the effective ingredient.

I claim:

1. A N-methyldeacetylcolchiceinamide derivative represented by the following formula or a salt thereof:

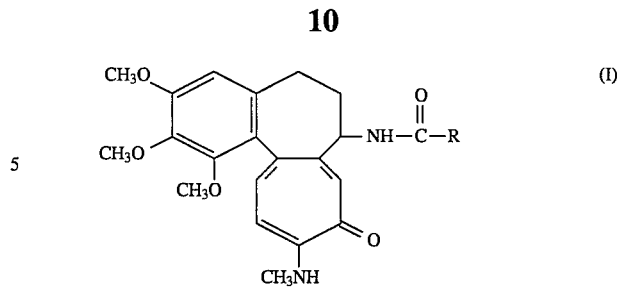

wherein R denotes a residue obtained by removing COOH from a carboxylic acid selected from the group consisting of glyceric acid, ribose carboxylic acid, glucuronic acid, gluconic acid and glucoheptanoic acid, and hydroxyl groups present in the residue are unprotected or protected with a hydroxyl-protecting group.

2. A N-methyldeacetylcolchiceinamide derivative of claim 1 wherein R is

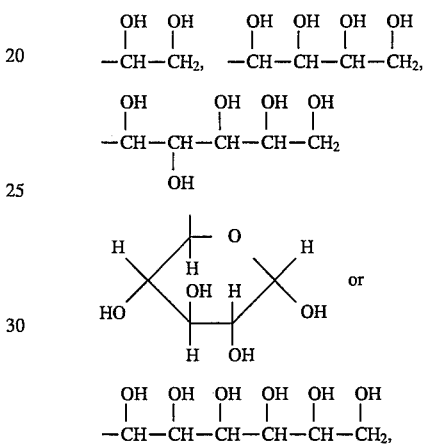

and the hydroxy groups present in these groups are unprotected or protected with an acyl group, an acetal group or a ketal group.

3. N'-(O,O-isopropylideneglyceroyl)-N-methyldeacetylcolchiceinamide.

4. A pharmaceutical preparation comprising an antitumor effective amount of an N-methyldeacetylcolchiceinamide derivative of the formula (I) recited in claim 1 or a pharmaceutically acceptable salt thereof, and pharmaceutically acceptable carrier or diluent.

5. A method for treatment of a leukemia which comprises administering atherapeutically effective amount of a N-methyldeacetylcolchiceinamide derivative of the formula (I) recited in claim 1 or a pharmaceutically acceptable salt thereof.

* * * * *